United States Patent [19]

Pásztor et al.

[11] Patent Number: 4,477,255

[45] Date of Patent: Oct. 16, 1984

[54] PHARMACEUTICALLY ACCEPTABLE SILICON RUBBER AND THERAPEUTICAL SET AND THE USE THEREOF FOR SURGICAL EMBOLIZATION

[76] Inventors: Emil Pásztor, 4, Rákóczi-u, Budapest, Hungary, 1072; László Lázár, 4, Rózsahegy-u, Budapest, Hungary, 1024; József Nagy, 46/b Törökbálinti-u, Budapest, Hungary, 1122; Katalin Pállosy née Becker, 31, Vincellér-u, Budapest, Hungary, 1113

[21] Appl. No.: 445,691

[22] Filed: Dec. 1, 1982

Related U.S. Application Data

[62] Division of Ser. No. 235,084, Feb. 17, 1981, Pat. No. 4,429,062.

[30] Foreign Application Priority Data

Feb. 18, 1980 [HU] Hungary ................................. 369/80

[51] Int. Cl.$^3$ ............................................ A61M 25/00
[52] U.S. Cl. ........................................ 604/97; 604/96; 128/658
[58] Field of Search ................ 523/118; 524/730, 731, 524/796, 863, 267; 528/33, 901; 604/96–103; 128/325, 656–658

[56] References Cited

U.S. PATENT DOCUMENTS

| | | | |
|---|---|---|---|
| 3,997,497 | 12/1976 | Itoh et al. | 528/33 |
| 4,104,239 | 8/1978 | Bargain et al. | 524/863 |
| 4,335,723 | 6/1982 | Patel | 604/97 |

Primary Examiner—C. Fred Rosenbaum
Assistant Examiner—Harrie S. Samaras
Attorney, Agent, or Firm—Toren, McGeady and Stanger

[57] ABSTRACT

A therapeutic set or kit containing a silicon rubber mixture for surgical embolization composed of (a) a linear, low viscosity polysiloxane selected from the group consisting of dialkyl, alkylaryl, alkenylalkyl, and diaryl polysiloxanes having reactive functional groups selected from the group consisting of hydroxy, acyloxy, alkoxy and amino;

(b) a cyclic dialkyl polysiloxane having the formula [R$_2$SiO]$_4$, wherein R is alkyl; and a pharmaceutically acceptable iodo-containing organosilicium X-ray contrast material or non-metallic organic X-ray contrast material. The mixture can be used in cerebrovascular surgery and general surgery for surgical embolization with the aid of a catheter.

2 Claims, No Drawings

PHARMACEUTICALLY ACCEPTABLE SILICON RUBBER AND THERAPEUTICAL SET AND THE USE THEREOF FOR SURGICAL EMBOLIZATION

This is a division of application Ser. No. 235,084, filed Feb. 17, 1981, U.S. Pat. No. 4,429,062.

The present invention relates to a new silicon rubber mixture, the use thereof for therapy as well as a therapeutic set or kit containing the said mixture. The new mixture and the therapeutic equipment can be used for the first time in the cerebrovascular surgery and general surgery, respectively, for surgical embolization by the aid of catheter.

The silicon rubber mixture of the present invention consists of two-three components, respectively, one of which gives X-ray contrast. The therapeutic set or kit according to the invention comprises the above silicon rubber mixture, the catalyst for the polymerization of the mixture, as well as a microcatheter provided balloon.

A further subject of the invention is the use of the new silicon rubber mixture and a therapeutic set, or kit respectively, on different fields of therapy, for the first time for cerebrovascular operations, vascular surgery, etc.

Due to their localization or size, certain parts of the human arterial system cannot be reached either via direct surgical exposure or endovascular approach i.e. by means of the generally used rigid "Seldinger type" catheters (secondary and tertiary arteries). This problem has been solved by the use of balloon catheters of a diameter less than 1 mm. Since these flexible catheters are provided with an inflatable natural rubber balloon head, they can utilize the so-called "parachute-effect" of the blood stream. These balloon-catheters have the importance for the cerebral endovascular surgery for the first time.

The cerebral arteries are surrounded by a stiff bony wall on the cranial base and have "syphons". Thus, the intracranial arteries became available only by using such catheters. The microcatheter filled with X-ray contrast medium, by means of fluoroscopic screen, gives the possibility to follow exactly the position of the balloon-head. When using two or special balloon catheters at the same time, the catheter can also be directed into the secondary arteries. The above method is, however, of diagnostic importance only, as when the catheter sent to its destination is left for blocking, it will also block the functionally important main vessels due to secondary thrombosis. This complication can be eliminated if the balloon were left in the vessels isolated, by detachment and withdrawing the catheter. The isolation and the so-called "superselective embolization is ensured by the physical possibility that the inflated balloon head is fixed to the inner wall of the vessel to be blocked stronger than the flexible connection between the balloon and the ending of the catheter. The detachment of the balloon head, filled with fluid, is, however, dangerous on the one hand as the balloon can leave its place, and on the other hand it can be unsuccessful as the fluid flows out of the balloon. Filling a quickly hardening fluid in the catheter ensures the stable fixing of the balloon in the vessel and a permanent, safe occlusion of the desired area.

The object of the present invention is to provide a novel and useful therapeutic set or kit equipment by the aid of which the above detachment and thus the embolization of certain vessels and permanent blocking of further ducts, respectively, can be performed easily and with great certainty without any problem at imparting the catheter.

The above balloon catheter method has been theoretically worked out recently by F. Sorbinenko [J. of Neurosurgery 41, 125–145 (1974)], no material has been found, however, by the aid of which the catheter could be detached effectively, moreover, in the absence of the contrast material the position of the catheter could not be followed.

P. Schaps in Zentralblatt für Neurochirurgie 38, 105–10 (1977) describes the use of silicon together with microcatheter and balloon, the viscosity of the material used was, however, so high that only ice-cooling technique could be applied, moreover, neither this material contained X-ray contrast material.

G. Debrun, P. Lacour, J. Caron et al. [J. of Neurosurgery 49, 635–49 (1978)] describes similar methods, they report, however, about difficulties in the impartation. In operations, detachment could be performed by using coaxial catheter, thus, the technique could not be used with safety for the intracranial vascular free operations.

S. K. Hilal, P. Sane, W. J. Michelson and A. Kossein, Neuroradiology 16, 430–33 (1978) describe the use of silicon elastomer (Silastic 382), methyl silicon oil and tantalum powder in the microcatheter technique. The disadvantage of the said mixture was the much higher viscosity than that good for an easy injecting, and on the other hand the use of tantalum powder, as X-ray contrast material obstructed the catheter by forming plugs. Moreover, the tantalum powder is toxic.

Summarizing, there was no material available which corresponded to all the requirements as discussed above. These requirements are as follows:

1. The low viscosity is very important: the material should be pressed through a catheter of 0.1 mm. inner diameter and 150 mm. length. This requirement is very hard to provide, considering that the fluid injected is to harden within a short period.
2. Due to the limited time for operation, the material should harden within a short time (i.e. 10 to 20 min.) so that sufficient time to inject the mixture (min. 3 to 4 min.) should also be provided.
3. The material should evenly fill in the catheter with sufficient plasticity so that no bubble is allowed to occur.
4. After hardening, however, the material should be rigid to a certain extent, i.e. it should break at the detachment.
5. It is very important for the precise dosing and control that the material should also give X-ray shadow. This characteristic provides that the position of the catheter and balloon, respectively, can be followed.
6. Sterility, no toxic effect.

The silicon rubber mixture provided by the invention, forming at the same time component A of the therapeutic set or kit fulfils all the above requirements.

The silicon rubber mixture of the present invention consists of an appropriate mixture of two different fluid polysiloxanes and a non-toxic, physiologically acceptable contrast material.

Thus, the silicon rubber mixture according to the invention consists of the following components:

(a) a linear polysiloxane of low viscosity, preferably e.g. the so-called reactive silicon oil, i.e. a dialkyl-, alkylaryl-, alkenylalkyl- or diarylpolysiloxane which may contain reactive functional terminal groups, i.e. hydroxy, acyloxy, alkoxy or amino. Preferred polysiloxane is the dimethyl-polysiloxane-α,ω-diol, the so-called "LMS". Physical data of the said compound are as follows:

$\bar{n} = 80-85$, $\bar{M} = 6-7000$, $d_4^{25°\ C.} = 0.976$ g./cm³., $n_D^{25°\ C.} = 1.4043$, 25° C. = 80-100 m.Pa.s. (cP).

(b) A cyclic dialkyl-polysiloxane, which has a very low viscosity. Such a cyclic dialkyl-polysiloxane derivative may be e.g. a dialkyl-polysiloxane, e.g. the so-called $D_4$ ($[R_2SiO]_4$) or $D_5$ ($[R_2SiO]_5$). For the purposes of the invention the $D_4$ is highly preferred. Its structure is $[(CH_3)_2SiO]_4$, the octamethyl-cyclo-tetrasiloxane, the physical data of which are as follows:

M = 296, b.p. = 175° C./0.1 MPa, $d^{20°\ C.} = 0.9558$ g./cm³., $n_D^{20°\ C.} = 1.3968$, 20° C. = 2 mPas (cP).

The viscosity of the mixture of the linear and cyclic polysiloxanes should be between n25° C. = 10 and 100 mPas, depending on the desired field of use.

(c) The mixture contains in a given case, methyl-silicon oil of a viscosity of 5 to 20 mPas which serves also the lowering of the viscosity.

(d) The fluid contrast material to be added to the mixture may be a physiologically acceptable silicium organic compound, which contains the iodine atom(s) giving the X-ray shadow built into the molecule. According to the invention, preferred contrast material is a bis-iodomethyl-tetramethyl-disiloxane. The iodine atom gives also the possibility of isotope labeling the material, when using e.g., I-131. The physical data of the said compound are as follows:

M = 414, b.p. = 134° C./1333.22 Pa, $d_4^{20} = 1.172$ g./cm³., $n_D^{20} = 1.5263$.

If mixtures of a viscosity of higher than 100 mPas may also be applied, non-metallic, iodine-containing organic X-ray contrast materials in extracted, solid, fine form may also be used. Such materials are used in the angiological diagnostics and are commercial products, i.e. Amipaque, Uromiro, etc. These materials are to be added to the components as above in a groundly homogenized form. Use of such materials, is, however difficult and requires more attention as the particle size should also be chosen in accordance with the field of application so that the particles should not obstruct the microcatheter and in case of free embolization they are not allowed to get into the capillary vascular system.

The silicon rubber system according to the invention, i.e. component of the therapeutic set or kit contains the linear polysiloxane under point (a) as above by all means while it should contain at least one of the materials under (b) and (d).

The therapeutic set or kit contains beside the component A mentioned above, the component B which can be any of the catalysts used for medical purposes in polymerizing cold-vulcanizing gums characterized by providing a fluidity of 8 to 10 mins and a hardening time of 20 to 25 mins.

It has been found that under the prescribed heat sterilizing conditions (120° C. for 30 mins) both components maintain the original chemical characteristics and abilities in the polymerization and the materials are acceptable in bacteriological aspects.

A further element of the therapeutic set or kit is the microcatheter. Depending on the field of use, it may contain one or more lumina. The therapeutic set or kit of the present, invention besides the components A and B and the microcatheter may also contain a balloon head made generally of natural index of silicone. This head has the importance in the first line at endovascular embolization wherein the silicon gum component is vulcanized in the balloon by the effect of the catalyst, thus forming a plug for blocking the said vessel. During free embolization, however, the use of balloon is not essential unless the wanted vascular area is not available otherwise.

The therapeutic set or kit can be used as follows:

The microcatheter, provided in a given case with the balloon at its end is led up to the target vessels or other duct-section. Then components A and B are mixed to provide a homogeneous mixture and the necessary amount is injected into the catheter through a calibrated tuberculin syringe. The injection is controlled by an X-ray fluoroscopic screen. After the rest of the material has hardened, the catheter is detached from the balloon head by a light, shifting pulling, subsequently the catheter is removed from the artery together with the silicon rubber vulcanized in the catheter.

Another object of the invention is the use of the said silicones and the mixture thereof for pharmaceutical purposes. The new material has been provided for the endovascular operation technique for the first time. The material and equipment may be used, however, in any case wherein no direct surgical intervention is possible or external operative approach of the concerned vessels is not advised.

The most important fields of the endovascular superselective embolization by means of balloon catheter are indicated among other as follows:

1. Blocking arteriovenous fistulas,
2. Embolization of arteriovenous angiomas,
3. Embolization of feeding arteries of highly vascularized tumors in order to promote the direct surgical removal of such neoplasms.
4. Endovascular occlusion of arterial saccular aneurisms.
5. Blocking oulet duct systems of different exocrin glands.

As mentioned, the embolization can be carried out by building the balloon into the vessel or other duct section to be blocked. The embolization may be performed, however, in the form of the so-called "free embolization" wherein the mixture of the components A and B acoording to the invention are injected directly into the pathological vascular area to be blocked, respectively, and the material is vulcanized in the vessel itself. It has been found that the materials and mixture of the invention are non-toxic either in themselves or during vulcanization. Thus, a further aspect of the present invention is the use of the materials and the mixture, respectively, described above, in the above free-embolization technique.

Based on animal tests, the above materials were used in about 30 successful human operations within a period of one and a half years in cases which could not be operated directly. It was proved that the hardened silicon remained in the natural rubber balloon resulted in definitive occlusion of the target spot. Following the X-ray shadow, the position of the balloon can be seen by a simple X-ray control even years after the operation. In case of free embolization the position of polymerized silicon rubber can also be controlled. It has also been found that the materials of the present invention, like other silicones widely used in surgery (i.e. ventriculo-atrial shunts, articular and other plastics, dental materials, etc.) are entirely compatible and non-toxic. No infection or abnormal histological reaction could be detected. Essentially it is the characteristic which makes possible the free embolization method described above.

In the following we give some possible examples for the silicon rubber mixture of the present invention.

EXAMPLE 1

10 g. of dimethyl-polysiloxane-$\alpha,\omega$-diol, viscosity 50 to 2000 mPas 1 g. of powdered, dried X-ray contrast material (UROMIRO), passed through a sieve of a size of 0.65 $\mu$m. The mixture is homogenized, and, before use, sterilized in vials. The catalyst, 1, 5 ccm of T-5 (Wacker dental catalyst product) is also sterilized in vial. Mixing of the two components provides a "batch-time" of 8 mins and a polymerization time of 15 mins. The catheter can be imparted after 15 to 25 mins.

EXAMPLE 2

Another possible component A is as follows:
10 g. of dimethyl-polysiloxane-$\alpha,\omega$-diol, viscosity 100 mPas,
2 g. of X-ray contrast material as in Example 1,
2 g. of methyl-silicon oil of dimethyl-polysiloxane basis, viscosity 19 mPas.

The component B and the amount thereof is the same as in Example 1.

EXAMPLE 3

Component A:
2.5 g. of dimethyl-polysiloxane-$\alpha,\omega$-diol, viscosity 100 mPas,
2.5 g. of $D_4$ (cyclic polysiloxane), viscosity 4-5 mPas,
0.75 g. of bis-iodomethyl-tetramethyl-disiloxane (fluid iodo-containing X-ray contrast material)

The mixture is homogenized, and then filled into vials and sterilized. As component B T-5 or T-11 catalysts (Wacker dental catalyst products) may be used in an amount of 1 ccm.

Clinical tests:

1. 35 year old man, miner. After craniocerebral trauma developed an extreme large fistula between the right internal carotid artery and cavernous sinus, resulted in typical eye-symptons, bruit, haedache, lesion of the right II., III., IV- and both VI. cranial nerves. Via percutan endovascular catheterization the fistula had been closed with 2 detached, siliconized balloons. Excellent clinical result, the patient is symptom-free even two years after the operation.

2. 25 year old man, electrotechnician. More severe subarachnoidal bleeding, resulted in transient unconsciouness and hemiplegia on the left. The angiographies proved a congenital arteriovenous malformation of the total right cerebral hemisphere. There was no possibility of direct surgical operation, because of the size of the angiom. Two main feeding arteries of the vascular malformation has been occluded with superselective balloon-embolization. Significant clinical improvement: the patient can walk done, free of mental disturbance, continues his original profession, got married, no more haemorrhages since the operations.

3. 53 years old woman, teacher. Giant saccular aneurysms on the cavernous portion of the left internal carotid artery, resulted in an earlier subarachnoidal haemorrhage and actually the lesion of the left III. cranial nerv. In order to the safe occlusion both the parent vessel and aneurysmal neck had to be embolized with a large balloon, filled with silicone. The transient postoperative hemiparesis and aphasia as well as the oculomotor paresis have improved, the patient is pratically free of symptoms after a period of a year and a half.

4. 24 old man. After frequent nasal haemorrhages and definitive obstruction of the nose a large-size haemangiom of the face had been proved histologically. Because of the size and localisation the direct surgical operation was unsuccessful. After the embolization of the feeding maxillar arterial branches succeeded in subtotal surgical removal of this benign tumor.

Although this method has been applied till present, when a direct surgical approach was impossible or more dangerous, there is a real possibility to extend the indication for the routine cases of the mentioned diseases too, with better results and lower hazard.

We claim:

1. A therapeutic set or kit containing a silicon rubber component A composed of a linear polysiloxane, a cyclic dialkyl-polysiloxane and a pharmaceutically acceptable iodo-containing organosilicium or non-metallic organic X-ray contrast material, a therapeutically acceptable cross-linking catalyst as component B, and a microcatheter.

2. The therapeutic set or kit of claim 1 having a balloon at the end of the catheter.

* * * * *